United States Patent [19]

Kawai et al.

[11] Patent Number: 4,948,783
[45] Date of Patent: Aug. 14, 1990

[54] ANTICARIOGENIC OR ANTIPERIDONTITIC METHOD

[75] Inventors: Yasuo Kawai, Atsugi; Kazuoki Ishihara, Tokyo, both of Japan

[73] Assignee: Kabushiki Kaisya Advance Kaihatsu kenkyujo, Tokyo, Japan

[21] Appl. No.: 275,625

[22] Filed: Nov. 15, 1988

Related U.S. Application Data

[63] Continuation of Ser. No. 824,560, Jan. 23, 1986, abandoned.

[30] Foreign Application Priority Data

Jan. 24, 1985 [JP] Japan .................................. 60-009948

[51] Int. Cl.$^5$ ...................... A61K 31/70; C07H 19/19; C07H 19/167
[52] U.S. Cl. ....................................... 514/46; 514/45; 536/24; 536/26

[56] References Cited

U.S. PATENT DOCUMENTS 3,475,408 10/1969 Kuhn et al. ............................ 536/26
4,374,822 2/1983 Fine et al. .............................. 424/49

FOREIGN PATENT DOCUMENTS 0184248 6/1986 European Pat. Off. .............. 514/46
0191561 8/1986 European Pat. Off. .............. 514/46
2354100 6/1975 France ................................... 536/26

OTHER PUBLICATIONS

Sigma Chemical Co., Price List, Feb. 1984, St. Louis, Mo., 63178.
Montgomery et al., J. Med. Chem., V17, 1197-1207, 1974.
Schlenk, Adv. in Enzymology, 54, 195-265 (1983).
Ishikawo, Chem. Abstr., vol. 104, No. 23, p. 629, No. 205873z, Jun. 9, 1986.
Schlenk, F., "Methylthioadenosine", Advances in Enzymology, vol. 54, pp. 195-265 (1983).
Efthymiou, C. and Hansen, P. A., "An Anticariogenic Analysis of Lactobacillus Acidophilus", J. Infect. Dis., vol. 110, pp. 258-267.
Chemical Abstracts, vol. 104, No. 23.
DE-A-617-590, (Laboratories Auclair), p. 1, ¶ ¶ 1 and 2.
FR-A-164-2 938 (Papierwerke Waldhof-Aschaffenburg AG) (GB-A-1422642), an English Language Counterpart of this French Patent.
J. Dent. Res., vol. 61, 1982, p. 206, No. 248, A. Al Abousy et al., "The Effects of Some Nucleotides on Dental Pulp".
Arch. Oral. Biol., vol. 24, No. 1, 1979, pp. 15-20, I. Laikko et al., "Adenosine Triphosphate in Normal and Carious Human Dentine".
Arch. Oral. Biol., vol. 24, No. 4, 1979, pp. 313-315, Y. Le Bell et al., "Adenosine-5'-Triphosphate Levels of the Human Tooth Pulp During Health and Disease".

Primary Examiner—John W. Rollins
Assistant Examiner—L. Eric Crane
Attorney, Agent, or Firm—Finnegan, Henderson, Farabow, Garrett & Dunner

[57] ABSTRACT

An anticariogenic or antiperiodontitic agent containing, as an active component, adenosine or its derivatives having an antibacterial activity against *Streptococcus mutans* or *Bacteroides gingivalis*. This anticariogenic or antiperiodontitic agent has strong inhibitory effects on the growth of *Streptococcus mutans* causing dental caries and *Bacteroides gingivalis* causing periodontitis and has neither influence on intestinal microflora nor any side-effects when orally administered.

2 Claims, No Drawings

ANTICARIOGENIC OR ANTIPERIDONTITIC METHOD

This application is a continuation of application Ser. No. 824,560, filed Jan. 23, 1986, now abandoned.

BACKGROUND OF THE INVENTION

1. Field of the Invention

The present invention relates to anticariogenic or antiperiodontitic products such as beverages and foods which contain adenosine and its derivatives and which have an anticariogenic or antiperiodontitic activity.

2. Description of the Related Art

Several kinds of antibiotics and other substances acting in a manner similar to anti-bacterial substances against *Streptococcus mutans* and *Bacteroides gingivalis*, which are major pathogens of dental caries and periodontitis, respectively, have been proposed. However, their side-effects, for example, the influence of these substances on intestinal microflora, are not yet fully understood, and accordingly, these substances are not used in practice since there is no proof that they are safe for daily usage.

SUMMARY OF THE INVENTION

Accordingly, the objects of the present invention are to eliminate the above-mentioned possible side-effects of the prior art and to provide an anticariogenic or antiperiodontitic agent or composition having strong inhibitory effects on the growth of *Streptococcus mutans* causing dental caries and *Bacteroides gingivalis* causing periodontitis and having no influence on intestinal microflora when orally administered.

Other objects and advantages of the present invention will be apparent from the following description.

In accordance with the present invention, there is provided an anticariogenic or antiperiodontitic agent or composition containing, as an active component, adenosine and its derivatives having antibacterial activity against *Streptococcus mutans* or *Bacteroides gingivalis*.

DESCRIPTION OF THE PREFERRED EMBODIMENT

The present inventors have found that adenosine and its derivatives have strong inhibitory effects on the growth of *S. mutans* causing dental caries and *B. gingivalis* causing periodontitis, but show no toxicity in animal experiments and no influence on intestinal microflora when orally administered.

The anti-bacterial products according to the present invention, the physiological characteristics thereof, the forms in practical use, and the like, will now be described in detail.

Antibacterial Product

Effective constituents of antibacterial products according to the present invention are adenosine and its derivatives. A particularly suitable example of such compounds is shown by the following chemical formula.

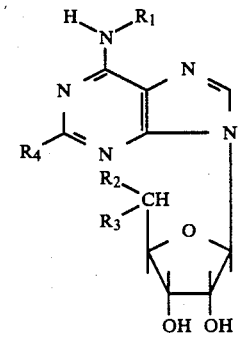

wherein $R_1$ is —H, —CH$_3$, or

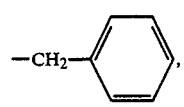

$R_2$ is —H, —OH, —Cl, —SCH$_3$, or —SCH$_2$CH(CH$_3$)$_2$, $R_3$ is —CH$_2$CH$_2$CH(NH$_2$)COOH or —H, and $R_4$ is —H or —Cl.

Typical examples of such compounds are vitamin L$_2$ (i.e., methylthioadenosine), 5'-deoxy-5'-chloroadenosine, N-6-methyladenosine, N-6-benzyladenosine, 2-chloroadenosine, 5'-deoxyisobutylthioadenosine, adenosine, and spongoadenosine (adenosine-9β-D-arabinofuranoside) which is an adenosine stereoisomer, and the like. Furthermore, S-adenosylmethionine is an example of a compound which can be easily decomposed to give vitamin L$_2$ and having antibacterial activity. These compounds are known and are commercially available. Furthermore, these compounds can be prepared in any conventional manner. For example, vitamin L$_2$ (methylthioadenosine (MTA)) is chemically synthesized as follows:

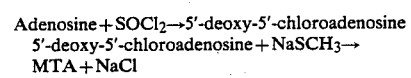

Adenosine+SOCl$_2$→5'-deoxy-5'-chloroadenosine
5'-deoxy-5'-chloroadenosine+NaSCH$_3$→MTA+NaCl These reactions are used for the preparation of vitamin L$_2$ (MTA) and many of its analogs (Schlenk, F., Methylthioadenosine In: Advances in Enzymology 54: 195–265 (1983)).

Physiological Characteristics

1. Antibacterial activity

As shown in the Examples below, the anticariogenic and antiperiodontitic products of the present invention effectively depress or inhibit the growth of *S. mutans* which cause dental caries and *B. gingivalis* which causes periodontitis.

2. Acute toxicity

As shown in the Examples below, an LD$_{50}$ value of the anticariogenic and antiperiodontitic products of the present invention is more than 1 g/kg body weight, orally administered to mice, and is substantially non-toxic on oral administration.

Forms in practical use

The anticariogenic and antiperiodontitic products of the present invention can be practically used in the form of, for example, tooth-paste, gargles, troches, chewing gum, and the like, and in the form of various kinds of anticariogenically and antiperiodontitically depressive and preventive foods and beverages added with the anticariogenic and antiperiodontitic products. The amount used in practical use is about 0.001% to 1% (w/w), based on the total weight of the composition.

Any conventional ingredients can be formulated into the present compositions. For example, in the case of tooth-pastes, ingredients such as secondary calcium phosphate (30-50%, w/w), glycerin (15-20%, w/w), carrageenan (0.5-20%, w/w), sodium lauryl sulfate as detergent (0.8-1.5%, w/w) and flavor (0.5-1.5%, w/w) can be added; in the case of gargles, ethanol (15-20%, w/w), saccharin (0.1-0.5%, w/w), sodium acyltaurate (0.2-0.6%, w/w), flavor (0.5-1.5%, w/w) and others can be added; and gum base (18-25%, w/w), calcium carbonate (1-5%, w/w), lactose (65-75%, w/w) and others can be added in the case of chewing gums. These additives are shown below in Examples in practical use.

EXAMPLES

The present invention will now be further shown by, but is no means limited to, the following Examples.

EXAMPLE 1

Antibacterial activity of vitamin $L_2$ (methylthioadenosine)

A sample of vitamin $L_2$ (methylthioadenosine) (Sigma Chemical Company) having the chemical formula shown below was dissolved in water,

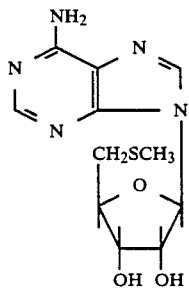

the pH was adjusted to 7, and sterilization was carried out by autoclaving at 121° C. for 15 min or by filtration with membrane filters, to form a sterile solution. This sample solution mentioned above was added into a sterile basal medium (refer to Table 1) together with sterile distilled water to adjust the concentration of the sample. To this medium, S. mutans causing dental caries, Actinomyces naeslundii and A. viscosus causing dental caries and periondontitis, and B. gingivalis and Fusobacterium nucleatum causing periodontitis, each bacterium being isolated from a human oral cavity, were repectively inoculated. After incubation at 37° C. for 24 hrs, the MIC (minimal growth-inhibitory concentration: μg/ml) against each bacterium was determined. As a control, a 0.85% NaCl solution was used instead of the sample solution of vitamin $L_2$. Furthermore, the effect of vitamin $L_2$ on intestinal bacteria such as S. faecium, S. faecalis, Bifidobacterium bifidum, Lactobacillus acidophilus, and L. fermentum, isolated from the feces of healthy humans, was also determined by the same procedures. The results are shown in Table 1.

TABLE 1

| | MIC (μg/ml) | Basal medium |
|---|---|---|
| S. mutans | 63 | Todd-Hewitt broth (Difco Laboratories) |
| A. naeslundii | 32 | Brain heart infusion broth (Difco Laboratories) |
| A. viscosus | 63 | Brain heart infusion broth |
| B. gingivalis | 125 | GAM broth (Nissui Pharmaceutical Co., Ltd.) |
| F. nucleatum | 500 | GAM broth |
| S. faecium | >1000 | Todd-Hewitt broth |
| S. faecalis | >1000 | Todd-Hewitt broth |
| Bif. bifidum | >1000 | GAM broth |
| L. acidophilus | >1000 | Rogosa broth *1 |
| L. fermentum | 1000 | Rogosa broth |

*1: Composition of Rogosa broth medium
Trypticase 10 g
Yeast extract 5 g
Tryptose 3 g
$K_2HPO_4$ 3 g
$KH_2PO_4$ 3 g
Triammonium citrate 2 g
Tween 80 *3 1 g
Glucose 20 g
Cysteine hydrochloride 0.2 g
Salt solution *2 5 ml
Distilled water to 1 liter
(pH 7, heat sterilization at 121° C. for 15 minutes)
*2: $MgSO_4.7H_2O$ 11.5 g
$FeSO_4.7H_2O$ 0.68 g
$MnSO_4.2H_2O$ 2.4 g
Distilled water 100 ml
*3: Polyoxyethylene (20) sorbitan monooleate available from Atlas Powder Co.

(Efthymiou, C., and Hansen, P. A. An antigenic analysis of Lactobacillus acidophilus. J. Infect. Dis. 110: 258-267 (1962))

EXAMPLE 2

Antibacterial activity of each adenosine derivative

The MIC (μg/ml) of seven kinds of adenosine derivatives (Sigma Chemical Company), having the chemical formulas as shown in Table 2, against S. mutans and B. gingivalis was determined by the same procedures as in Example 1. The results are shown in Table 3.

TABLE 2

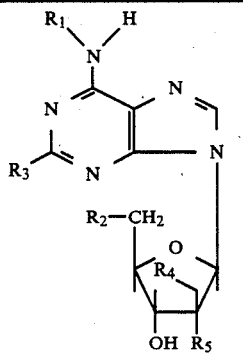

| Materials | $R_1$ | $R_2$ | $R_3$ | $R_4$ | $R_5$ |
|---|---|---|---|---|---|
| (1) 5'-deoxy-5'-chloroadenosine | —H | —Cl | —H | —H | —OH |
| (2) N-6 methyladenosine | —CH$_3$ | —OH | " | " | " |
| (3) N-6 benzyladenosine | —CH$_2$—C$_6$H$_5$ | " | " | " | " |
| (4) 2-chloroadenosine | —H | " | —Cl | " | " |
| (5) (5'-deoxy) isobutylthioadenosine | " | —SCH$_2$CH(CH$_3$)$_2$ | —H | " | " |
| (6) adenosine | " | —OH | " | " | " |
| (7) spongoadenosine | " | " | " | —OH | —H |
| (8) 5'-deoxyadenosine | " | —H | " | —H | —OH |

TABLE 3

| Materials No. | Bacteria | |
|---|---|---|
| | S. mutans | B. gingivalis |
| (1) | 250 | 125 |
| (2) | 1000 | 250 |
| (3) | 1000 | 250 |
| (4) | 1000 | 250 |
| (5) | 1500 | 250 |
| (6) | 1000 | No inhibition |
| (7) | 1500 | 16 |
| (8) | 1000 | 125 |

EXAMPLE 3

Acute toxicity

The above adenosine derivatives were orally administered to ICR mice (6 week-old, male, average body weight of 31.0±0.6 g, 10 mice per group) in the form of a 0.5 ml saline solution having the equivalent amounts of the derivatives of 1, 10, 100 mg/mouse. The sanatobiological observation of the mice was carried out for 14 days.

The LD$_{50}$ values (mg/kg body weight) calculated according to the Behrens-Kärber method were more than 1000 mg/kg body weight, but were substantially nontoxic in the case of daily oral administration.

| Examples in practical use | |
|---|---|
| 1. Tooth-paste | Wt. % |
| Secondary calcium phosphate | 30–50 |
| Glycerin | 15–20 |
| Carrageenan | 0.5–20 |
| Sodium lauryl sulfate | 0.8–1.5 |
| p-Oxybutyl benzoate | 0.001–0.005 |
| Flavor | 0.5–1.5 |
| Antibacterial products of the present invention | 0.01–5 |
| | 100 |

| Examples in practical use | |
|---|---|
| 2. Gargles | |
| Ethanol (90%) | 15–20 |
| Saccharin | 0.1–0.5 |
| Sodium acyltaurate | 0.2–0.6 |
| Gelatin | 0.1–0.6 |
| Flavor | 0.5–1.5 |
| Chlorohexidine | 0.002–0.007 |
| Antibacterial products of the present invention | 0.01–5 |
| Water | Remainder |
| | 100 |

| 3. Chewing gum | |
|---|---|
| Gum base | 18–25 |
| CaCO$_3$ | 1–5 |
| Saccharin | 0.05–0.2 |
| Lactose | 65–75 |
| Antibacterial products of the present invention | 0.001–0.5 |
| | 100 |

4. Anticariogenic foods and beverages

The antibacterial products of the present invention can be used for anticariogenic or antiperiodontitic foods and beverages by the addition of 0.001% to 1% by weight (dry weight) of the products into bread, cookies, candies, yogurt, fruit juice, tea, coffee, etc., and other general foods and beverages.

We claim:

1. A method of preventing or treating dental caries or periodontitis which comprises orally administering to a host susceptible to or in need thereof a composition comprising:
   (a) an effective amount of adenosine or its derivatives having the general formula:

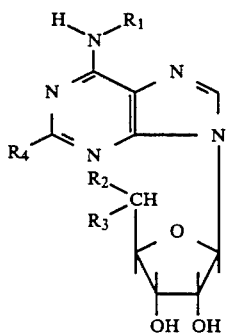

wherein $R_1$ is —H, —CH$_3$, or

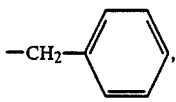

$R_2$ is —H, —OH, —Cl, —SCH$_3$, OR —SCH$_2$CH(CH$_3$)$_2$; $R_3$ is —H or —CH$_2$CH$_2$CH(NH$_2$)COOH, and $R_4$ is —H or —Cl, and having antibacterial activity against *Streptococcus mutans* or *Bacteriodes gingivalis*, and (b) an orally acceptable carrier therefor.

2. A method as claimed in claim 1, wherein said adenosine or its derivative is at least one compound selected from the group consisting of methylthioadenosine, 5'-deoxy-5'-chloroadenosine, N-6-methyladenosine, N-6-benzyladenosine, 2-chloroadenosine, 5'-deoxyisobutylthioadenosine, adenosine, spongoadenosine, and S-adenosylmethionine.

* * * * *